United States Patent [19]

Hopp

[11] Patent Number: 5,019,383
[45] Date of Patent: May 28, 1991

[54] FATTY ACID CARRIERS FOR SYNTHETIC PEPTIDES

[75] Inventor: Thomas P. Hopp, New York, N.Y.

[73] Assignee: New York Blood Center, Inc., New York, N.Y.

[21] Appl. No.: 405,102

[22] Filed: Sep. 8, 1989

Related U.S. Application Data

[63] Continuation of Ser. No. 942,562, Dec. 16, 1986, abandoned, which is a continuation of Ser. No. 358,150, Mar. 15, 1982, abandoned, which is a continuation-in-part of Ser. No. 223,558, Jan. 9, 1981, abandoned, which is a continuation-in-part of Ser. No. 272,855, Jun. 12, 1981, abandoned.

[51] Int. Cl.$^5$ ............................................. A61K 39/00
[52] U.S. Cl. ...................................... 424/88; 530/406; 530/345
[58] Field of Search .................. 530/406, 345; 424/88

[56] References Cited

U.S. PATENT DOCUMENTS

| | | | |
|---|---|---|---|
| 3,985,722 | 10/1976 | Yoshida et al. | 530/360 |
| 4,284,537 | 8/1981 | Beuchey | 260/6 |
| 4,401,658 | 8/1983 | Bouchaudon et al. | 530/331 |
| 4,415,491 | 11/1983 | Vyas | 260/112.5 |

FOREIGN PATENT DOCUMENTS

| | | |
|---|---|---|
| 0044710 | 1/1982 | European Pat. Off. . |
| 0056249 | 7/1982 | European Pat. Off. . |
| 2349569 | 11/1987 | France . |
| WO8204250 | 12/1987 | PCT Int'l Appl. . |

OTHER PUBLICATIONS

Parsons, Peptide Hormones (1976) Chapter I pp. 2–7.
Proc. Natl. Acad. Sci. U.S.A., vol. 79, No. 2, Jan. 1982, pp. 579–582, Immunology; A. M. Prince et al.: "Hepatitis B Virus Vaccine: Identification of HBsAg/a and HBsAg/d but not HBsAg/y Subtype Antigenic Determinants on a Synthetic Immunogenic Peptide".
Proc. Natl. Acad. Sci. U.S.A., vol. 79, No. 14, Jul. 1982, pp. 4400–4404, Immunology; P. K. Bhatnagar et al:
"Immune Response to Synthetic Peptide Analogues of Hepatitis B Surface Antigen Specific for the a Determinant".
Thomas P. Hopp. Immunogenicity of a Synthetic HBsAg Peptide: Enhancement by Conjugation to a Fatty Acid Carrier, Molecular Immunology, vol. 21, No. 1, pp. 13–16, 1984.
Stark et al., Immunology vol. 39, pp. 345–352, 1980 "Immunogenicity of Lipid Conjugated Antigens. I, The Influence of Chain Length and Degree of Conjugation on Indulation of Antibody in Mice".
Hopp, Thomas Proc. Nat'l Acad. Sci. vol. 78, No. 6, pp. 3824–3828 (Including Kenneth R. Woods) "Prediction of Protein . . . ".
Hopp, Thomas Dissertation Abstracts International Nov., 1977 Abstract 2155b.
Walter et al., Proc. Nat'l Acad. Sci. vol. 17, No. 9 Sep. 80, pp. 5197–5200 "Antibodies . . . Large Tumor Antigen".
Arnon, Ruth Pharmac. Ther. vol. 6, 1979, "Anti-Viral Activity Induced by Synthetic Peptides . . . ".
Walter et al., Proc. Natl. Acad Sci. U.S.A., vol. 77, No. 9 5197–5200, Sep. 1980.
Satcliffe et al., Nature, vol. 287, pp. 801–805, Oct. 30, 1980.

Primary Examiner—Lester L. Lee
Assistant Examiner—Susan H. Perkins
Attorney, Agent, or Firm—Sprung, Horn, Kramer & Woods

[57] ABSTRACT

A synthetic vaccine is contemplated comprising a peptide residue coupled to one or more alkyl or alkenyl groups of at least 12 carbon atoms or other lipophilic substance wherein said peptide residue contains a sequence of 6 amino acids corresponding to the sequence of such amino acids in a protein antigen or allergen where the greatest local average hydrophilicity of the antigen or allergen is found.

21 Claims, No Drawings

FATTY ACID CARRIERS FOR SYNTHETIC PEPTIDES

CROSS REFERENCE TO RELATED APPLICATIONS

This application is a continuation of Ser. No. 06/942,562, filed Dec. 16, 1986, now abandoned, which is a continuation of Ser. No. 06/358,150, filed Mar. 15, 1982, now abandoned, which is a continuation-in-part of Ser. No. 06/223,558, filed Jan. 9, 1981, now abandoned, which is a continuation-in-part of Ser. No. 06/272,855, filed June 12, 1981, now abandoned.

BACKGROUND OF THE INVENTION

1. Field of the Invention

This invention is directed to a synthetic vaccine, to a composition useful in elliciting formation of antibodies in a host animal and to a composition useful as a diagnostic aid. More especially this invention is directed to a synthetic antigenic composition comprising a synthetic peptide and carrier. Still more especially this invention is directed specifically to the nature of the carrier for the synthetic peptide.

2. Discussion of Related Applications

In my co-pending applications referred to above I disclosed a new system for determining that portion of the protein of a natural antigen or allergen which is responsible for the antigenicity or allergenicity of the protein. More especially I defined a process for determining the specific sequences of amino acid of proteinaceous allergens or antigens which are causative of an immune response when compositions containing the same are injected into host animals.

Thus I disclose not only that method for determining the specific sequence of amino acids but a method of preparing synthetic antigens or allergens knowing the precise number and sequence of amino acids which must be present. I also disclose numerous synthetic vaccines comprising a short polypeptide supported on a carrier, the carrier considered to be of critical importance in providing the active portion of the synthetic peptide chain with sufficient size so that the entire synthetic antigen or synthetic allergen can be recognized by the immune system and evoke formation of the corresponding antibodies.

Specifically, my synthetic vaccine comprises a physiologically acceptable carrier in or on which is disposed a synthetic peptide residue containing a sequence of at least six amino acids corresponding to the sequence of such amino acids in a protein antigen or allergen with the greatest local average hydrophilicity of the antigen or allergen, said local hydrophilicity of said protein antigen or allergen being defined by and determined by:

A. assigning relative hydrophilicity values to the amino acids of the protein antigen or allergen in accordance with relative relationship of such amino acids as shown in the table below:

TABLE 1

| Amino Acid | Hydrophilicity Value |
|---|---|
| Arginine | 3.0 |
| Aspartic Acid | 3.0 ± 1 |
| Glutamic Acid | 3.0 ± 1 |
| Lysine | 3.0 |
| Serine | 0.3 |
| Asparagine | 0.2 |
| Glutamine | 0.2 |
| Glycine | 0.0 |
| Proline | −.5 ± 1 |
| Threonine | −0.4 |
| Alanine | −0.5 |
| Histidine | −0.5 |
| Cysteine | −1.0 |
| Methionine | −1.3 |
| Valine | −1.5 |
| Isoleucine | −1.8 |
| Leucine | −1.8 |
| Tyrosine | −2.3 |
| Phenylalanine | −2.5 |
| Tryptophan | −3.4 |

B. determining the repetitive local average of hydrophilicity values at a plurality of points along the amino acid sequence:

C. determining from such local points of repetitive averages the points of greatest local average hydrophilicity; said composition being characterized by evoking a protective immunological response or by stimulation of antibody formation or decreased sensitivity to allergen when introduced into a host animal in the absence of the entire amino acid sequence of the protein antigen or allergen.

At the heart of the development there is the determination of a sequence of six amino acids which are critical to the production of the immunological response. In accordance with such earlier invention this is done with the foreknowledge of the amino acid sequence of an antigen or allergen, but if the same is unknown, then the amino acid sequence of the entire protein must first be determined. This can be done by known but laborious means.

Given the amino acid sequence of the entire protein antigen or allergen, the next objective is to determine the point along said molecule where there is greatest local average hydrophilicity. This is initially done by assigning relative hydrophilicity values in accordance with the table above to each amino acid in the protein. Thereafter, those values are repetitively averaged along the length of the protein. While such method is partially successful (working for some proteins, but not others) when averaging groups range in size from four to ten successively connected amino acids, it is preferred that in determining such local averages the hydrophilicity values of five to seven linearly connected amino acids be employed, especially six such amino acids. At a plurality of points along the amino acid chain of the protein, the local averages are determined (moving average, increment of one).

Once the repetitive local averages of the specific hydrophilicity values are determined, the precise point of greatest hydrophilicity can be easily located by inspection or determined graphically or otherwise. It has been discovered that the six amino acids providing the greatest local average hydrophilicity are the sequence of six amino acids which are critical to the production of the immunological response. Stated differently, it has been found that this sequence of six amino acids is present in an epitope of the protein, i.e. the sequence of amino acids recognized by and bound by an antibody with immunological specificity. Such epitope, is hereinafter designated as the "H-epitope" as it is the epitope of greatest local average hydrophilicity.

With this realization of the precise sequence of amino acids which accounts for H-epitope of a given protein antigen or allergen, one can form a synthetic vaccine in any number of ways.

The synthetic vaccine is prepared either by chemically synthesizing a chain of amino acids corresponding to the sequence of amino acids of the H-epitope or the H-epitope is obtained from a protein containing the same by selective lysis such as by splitting the protein by the use of enzymes. The amino acid chain containing the H-epitope so obtained either synthetically or from naturally occurring protein is thereafter disposed on a physiologically acceptable carrier, and the resultant composition is thereafter diluted with physiologically acceptable medium. The composition is then ready for introduction into a host animal.

It will be realized that the process of the invention is useful in the formation of synthetic vaccines of known and unknown, identified or unidentified, protein antigens or allergens, since the focus is upon the portion of the protein molecule which provides the H-epitope. Thus, the synthetic vaccine of the invention can contain H-epitopes of single or multiple known or unknown protein antigens or allergens. The synthetic vaccine can contain a plurality of H-epitopes of a single antigen or can contain a single H-epitope of a first antigen and an H-epitope of a second antigen or allergen. The synthetic vaccine can contain one or more H-epitopes of an antigen or allergen alone or in combination with one or more H-epitopes of a second antigen or allergen. In fact, the synthetic vaccine can contain as may epitopes corresponding to said sequence of six amino acids of greatest local average hydrophilicity as desired, and said epitopes can correspond to the sequence of six amino acids from a wide variety of antigens or allergens. The vaccine contains at least one H-epitope. This H-epitope can be co-present with other epitopes of the same or different antigens which are not H-epitopes, i.e., do not correspond to the point of greatest local average hydrophilicity of the antigen or allergen.

The process of the invention is useful in the formation of synthetic vaccines from antigens whose amino acid sequence has not heretofore been reported. The art well knows how to determine the amino acid sequence of a protein antigen or allergen. It remains, therefore, a simple matter in accordance with the invention to determine the H-epitope.

The synthetic vaccine can have H-epitopes of any protein antigen or allergen. The vaccine of the following protein antigens or allergens are particularly contemplated. Hepatitis B surface antigen, histocompatibility antigens, influenza hemagglutinin, fowl plague virus hemagglutinin, rag weed allergens $Ra_3$ and $Ra_5$ and the antigens of the following viruses: vaccinia, Epstein-Barr virus, polio, rubella, cytomegalovirus, small pox, herpes, simplex types I and II, yellow fever, and many others.

It can also alternatively or additionally have and H-epitope of a protein of any of the following parasites: organisms carrying malaria (P. Falciporum, P. Ovace, etc.). Schistosomiasis, Onchocerca Volvulus and other filiarial parasites, Trypanosomes, Leisbmania, Chagas disease, amoebiasis, hookworm, and the like. In addition, vaccines of the following bacterial are especially contemplated: leprosy, tuberculosis, syphilis, gonorrhea and the like.

Vaccines of the following viruses can be made by the process of the invention: Infectious ectromelia virus, Cowpox virus, Herpes simplex virus Infectious bovine rhinotracheitis virus, Equine rhinopneumonitis (equine abortion) virus, Malignant catarrh virus of cattle, Feline rhinotracheitis virus, Canine herpesvirus, Epstein-Barr virus (ass, with infectious mononucleosis and Burkitt lymphoma), Marek's disease virus, Sheep pulmonary adenomatosis (Jaagziekte) virus, Cytomegaloviruses, Adenovirus group, Human papilloma virus, Feline panleucopaenia virus, Mink enteritis virus, African horse sickness virus (9 serotypes), Blue tongue virus (12 serotypes), Infectious pancreatic necrosis virus of trout, Fowl sarcoma virus (various strains), Avian leukosis virus, visceral, Avian leukosis virus, erythroblastic, Avian leukosis virus, myeloblastic, Osteopetrosis virus, Newcastle disease virus, Parainfluenza virus 1, Parainfluenza virus 4, Mumps virus, Turkey virus, CANADA/58, Canine distemper virus, Measles virus, Respiratory syncytial virus, Myxovirus, Type A viruses, such as Human influenza viruses, e.g. Ao/PR8/34, Al/CAM/46, and A2/Singapore/1/57; Fowl plague virus; Type B viruses e.g. B/Lee/40; Rabies virus; Eastern equinine encephalitis virus; Venezuelan equine encephalitis virus; Western equine encephalitis virus; Yellow fever virus, Dengue type 1 virus (=type 6), Dengue type 2 virus (=type 5); Dengue type 3 virus; Dengue type 4 virus; Japanese encephalitis virus, Kyasanur Forest virus; Louping ill virus; Murray Valley encephalitis virus; Omsk haemorrhagic fever virus (types 1 and 11); St. Louis encephalitis virus; Human rhinoviruses, Foot-and-mouth disease virus; Poliovirus type 1; Enterovirus Polio 2; Enterovirus Polio 3; Avian infectious bronchitis virus; Human respiratory virus; Transmissible gastro-enteritis virus of swine; Lymphocytic choriomeningitis virus; Lassa virus; Machupo virus; Pichinde virus; Tacaribe virus; Papillomavirus.

Similarly, the synthetic vaccine can have an H-epitope of any protein allergen such as the rag weed allergens.

It is to be understood that the foregoing lists are not all-inclusive, but simply exemplary, since the heart of the invention resides in reliably and confidently predicting and determining the H-epitope.

In forming a synthetic vaccine according to the earlier invention, it is preferred to insure that the epitope has the steric configuration to be recognized by an antibody; that the given sequence of 6 amino acids have bonded thereto as part of the amino acid chain at least three amino acids on either side thereof, these three adjacent amino acids serving as auxiliary acids to insure the stabilization of the epitope so that it is readily recognized by and neutralized by an antibody.

In one of its simplest forms, that invention comprises a physiologically acceptable carrier on which is disposed a synthetic peptide residue of the designated epitope. This synthetic peptide residue has a chain length of minimally six amino acids, preferably twelve amino acids (considering the three amino acids on either side thereof) and can contain an infinitely long chain of amino acids or their components, which can be characterized by the presence of other epitopes of the same or different antigen or allergen. Where it is free of such additional chain with or without such additional epitopes, it generally does not have an amino acid chain exceeding 50 amino acids. Where a short chain is desired containing the desired epitope, it preferably does not have an amino acid chain length greater than 40, more especially not greater than 30 and more particularly not greater than 20 amino acids. Optimally the peptide residue has an amino acid chain length of 12 to 18 amino acids, preferably 12 to 15 amino acids, especially 12 amino acids.

In my earlier application I disclose numerous physiologically acceptable carriers for the peptide residue including those which are animal, vegetable and mineral. Specifically disclosed carriers included segments of polyamino acid, polysaccharides, polyamides, vinyl polymers, ester polymers, as well as proteins especially subclass hemoglobin, human serum proteins, tetanus toxoid.

One problem that exists in the field of vaccines relates to the nature of the carrier. Since optimally the vaccine stimulates production of only those antibodies specific to the antigen or allergen, the carrier should not evoke antibody formation to itself. The production of antibodies or any other substance in response to the carrier portion of the vaccine complicates the immune system's behavior, can be the cause of side reactions, and can compete with the production of antibodies to the synthetic antigen or allergen. It has therefore been desirable to provide a carrier for a synthetic vaccine where the carrier portion of the molecule is substantially inert to the immune system and does not evoke the production of antibodies specific thereto. It is the further object of this invention to provide an improved synthetic vaccine comprising a synthetic peptide residue disposed in or on a carrier where the carrier is one which is compatible with the organism into which the vaccine is to be introduced and can be readily metabolized by such host animal and in time be excreted without complications to the injection site or the various organs of the body.

SUMMARY OF THE INVENTION

In accordance with this invention I provide an improved synthetic antigen or synthetic allergen of the type disclosed in the aforementioned applications for Letters Patent wherein the carrier is one comprising a straight or branched substituted or unsubstituted, saturated or unsaturated hydrocarbon residue of at least twelve carbon atoms. In particular, the carrier of the invention is one having at least twelve carbon atoms in a chain whose chain is either an alkyl or alkenyl group. Such alkyl or alkenyl group can have up to 36 carbon atoms but is preferably in the range of $C_{12}$ to $C_{24}$. These hydrocarbon residues can be provided by fatty acids by simple coupling of the fatty acid moiety to a terminal functional group of the synthetic peptide by relatively routine chemistry. I also contemplate, however, carrying the synthetic residue on such hydrocarbon residues without the use of the carboxylic acid functional group of the fatty acid whereby the synthetic peptide is joined to the hydrocarbon residue without a carbonyl connecting link.

Thus, my invention can be described broadly as a composition comprising a synthetic antigen or allergen of the formula:

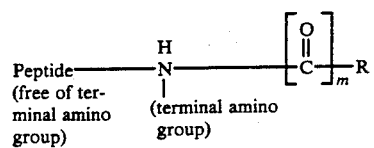

(I)

wherein
m is 0 or 1;

R is a substituted or unsubstituted alkyl or alkenyl radical of at least 12 carbon atoms; and Peptide is a residue containing a sequence of 6 amino acids corresponding to the sequence of such amino acids in a protein antigen or allergen where the greatest local average hydrophilicity of the antigen or allergen is found, said local hydrophilicity of said protein antigen or allergen determined by:

A. assigning relative hydrophilicity values to the amino acids of the protein antigen or allergen in accordance with relative relationship of such amino acids as shown in the table below:

TABLE 1

| Amino Acid | Hydrophilicity Value |
| --- | --- |
| Arginine | 3.0 |
| Aspartic Acid | 3.0 ± 1 |
| Glutamic Acid | 3.0 ± 1 |
| Lysine | 3.0 |
| Serine | 0.3 |
| Asparagine | 0.2 |
| Glutamine | 0.2 |
| Glycine | 0.0 |
| Proline | −.5 ± 1 |
| Threonine | −0.4 |
| Alanine | −0.5 |
| Histidine | −0.5 |
| Cysteine | −1.0 |
| Methionine | −1.3 |
| Valine | −1.5 |
| Isoleucine | −1.8 |
| Leucine | −1.8 |
| Tyrosine | −2.3 |
| Phenylalanine | −2.5 |
| Tryptophan | −3.4 |

B. determining the repetitive local average of hydrophilicity values at a plurality of points along the amino acid sequence.

C. determining from such local points of repetitive averages the points of greatest local average hydrophilicity; said synthetic antigen or allergen when free of an amino acid sequence corresponding to the entire protein antigen or allergen evoking a protective immunological response or stimulating antibody formation for decreasing sensitivity to allergen when introduced into a host animal, in the absence of the entire amino acid sequence of the protein antigen or allergen.

Referring to the formula above I can couple the synthetic peptide moiety to an alkyl or alkenyl group of at least 12 carbon atoms by blocking all those amino groups of the synthetic peptide residue so that they are free of reactivity to a carboxylic acid except that a terminal amino group remains available for reaction. I thereafter react the terminal amino group of the synthetic peptide with a moiety which supplies a carboxylic acid group whereby condensation of a hydrogen atom of the amino group with the hydroxyl group of carboxylic acid group (dehydration) effects interlinkage of the synthetic peptide with the carboxylic acid group in accordance with the following equation:

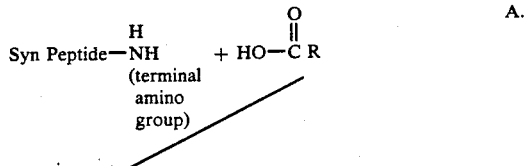

A.

-continued

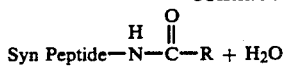

In accordance with this reaction there is formed a composition as defined in equation I above wherein m=1. I also envisage, however, disposing these synthetic peptides on a $C_{12}$–$C_{36}$ alkyl or alkenyl moiety without using a carboxylic acid or similar functional group to link with the terminal amino group. Thus for instance I envisage a substitution reaction in accordance with the following equation:

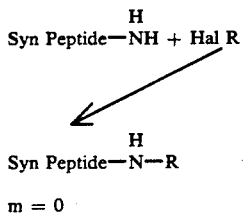

B.

$m = 0$ in which case there is formed a synthetic vaccine within formula I above wherein m is 0. Numerous alternative routes to disposing a synthetic peptide on a $C_{12}$ to $C_{36}$ alkyl or alkenyl group are apparent; these invariably linking the synthetic peptide to the alkyl or alkenyl moieties via a terminal amino group of the synthetic peptide moiety.

In forming a synthetic vaccine in accordance with this invention, I prefer to use a fatty acid of $C_{12}$ to $C_{24}$. Particularly contemplated fatty acids include the following:

Palmitic
Stearic
Behenic
Oleic.

The Merrifield solid phase synthesis for synthetic peptides is a particularly desirable approach to formation of a fatty acid carried synthetic peptide, since it provides a convenient means for attachment of the carrier in accordance with the invention, although it should be understood that liquid phase approaches can also be employed. The Merrifield solid phase approach involves connecting amino acids to one another where the pendent reactive groups, e.g., amino, hydroxyl, carboxyl, imidazol groups, are blocked. After the final amino acid has been coupled, the N-terminus is deblocked and a fatty acid or other suitable large lipophilic substituent or component supplying a $C_{12}$ to $C_{36}$ alkyl or alkenyl group is reacted by procedures outlined above for use in amino acid couplings, the procedure is carbodiimide mediated peptide (amide) bond formation, hydroxybenzotriazole ester addition or addition of a fatty acid symmetrical or asymmetrical anhydride.

This results in a peptide with covalent N-terminal fatty acid or similar moiety. The peptide is then removed from the resin by typical hydrofluoric acid treatment, and purified if necessary.

Such a fatty acid peptide conjugate is complete in and of itself and needs no additional carrier molecule or support for immunological enhancement. It aggregates when placed in aqueous medium and the aggregate is capable of stimulating a strong immune response similar to those achieved with carriers such as red blood cells or large proteins. Carriers of the invention, it is believed, are more suitable than carriers such as red blood cells and large proteins as the latter carriers tend to prompt unwanted immune responses directed against the carrier per se. Thus, carriers of the invention provide effective and readily produced vaccines with minimal chance of unwanted immunological responses.

Particularly contemplated reactants include fatty acid anhydrides of the formula:

wherein $R_1$ and $R_2$ are independently alkyl or alkenyl, including alkenyl containing multiple unsaturation of several carbon atoms. However, symmetric saturated alkyl $R_1$ and $R_2$ groups are preferred. These fatty acid anhydrides react relatively readily with the peptide. Generally speaking, reaction is effected at a temperature of between 20° and 30° for between 2 and 4 hours. The reaction is performed in the presence of a solvent. Particularly contemplated solvents include: methylene chloride, dimethylformamide or dimethylsulfoxide. Thereafter the peptide linked to the $C_{12}$ to $C_{36}$ alkyl or alkenyl group via amide moiety is removed from the Merrifield resin and the blocking agents are removed from the side chain groups by contacting the same with a strong acid such as: hydrofluoric, hydrobromic or methanesulfonic acids. Thereafter the material is worked up in the usual manner or washed and the synthetic vaccine is recovered.

The peptide can be carried on a $C_{12}+$ alkyl or alkenyl containing carrier which comprises a plurality of $C_{12}+$ alkyl or alkenyl moieties. Thus there is contemplated a synthetic antigen or allergen of the formula

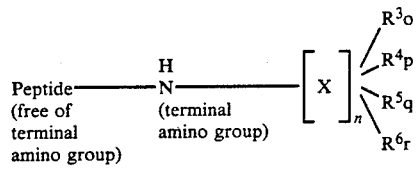

wherein
$R^3$, $R^4$, $R^5$, $R^6$ are each $C_{12}$–$C_{36}$ alkyl or alkenyl groups which may be straight or branched chained and substituted or unsubstituted;

o, p, q and r are each 0 or 1 and the sum of o, p, q and r is equal to n;

n is 2–4.

X is a polyfunctional group having 3 to 5 functional groups, at least one of which is bound to said terminal amino group, and at least one of said functional groups bound to one of $R^3$, $R^4$, $R^5$ or $R^6$.

Functional groups for X include carbonyl and amido. The carbonyl group is effective as a link to the terminal amino group whereby an amido group is formed while the amido group is an effective link between the synthetic peptide and the $C_{12}$–$C_{36}$ alkyl or alkenyl group.

The functional groups can be separated by a backbone which itself is an alkyl or alkenyl group, usually of chain length of 2 to 5 carbon atoms. Thus X can be represented by the formula

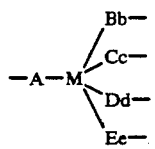

(III)

where

A is a bifunctional group one end of which is linked to M and the other end of which is linked to the terminal amino group of the synthetic peptide;

M is alkylene or alkenylene of 2 to 5 carbon atoms;

B, C, D and E are each bifunctional groups one end of which is linked to M and the other end of which is linked to a $C_{12}$–$C_{36}$ alkyl or alkenyl group and b, c, d, and e are each 1 or 0 and the sum of b, c, d and e is 2–4.

Specifically, such a structure can be provided using an amino acid having a plurality of amino groups. These amino groups are reactable with a source of $C_{12}$–$C_{36}$ alkyl or alkenyl groups. The synthetic peptide's side chain reactive groups are blocked with, for instance, a blocking agent of the type described above. The terminal amino group of the synthetic peptide is reacted with the multifunctional group or amino acid whereby the peptide now is joined to a bridge having two or more reactive sites to which $C_{12}$–$C_{36}$ alkyl or alkenyl groups can be bound. Thereafter the peptide-bridge intermediate structure is reacted with the source of $C_{12}$–$C_{36}$ alkyl or alkenyl groups.

The above embodiment can be described in terms of using an amino acid possessing a side chain and a terminal amino group.

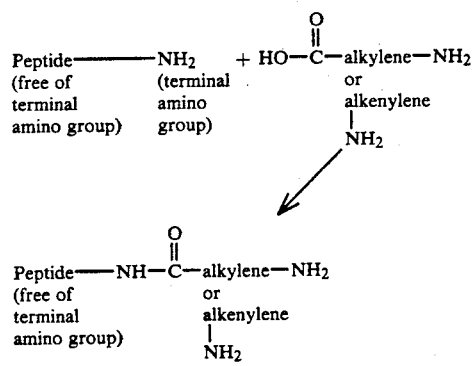

The two free —NH$_2$ groups remain reactive to source of $C_{12}$–$C_{36}$ alkyl or alkenyl groups. Usually the preparation of the intermediate involves the reaction of the terminal amino group of the peptide with such an amino acid where amino groups are protected by a functional group that is more readily removed than the side chain protecting groups of the peptide. Such protective but reactive groups include:

Tertiary butyloxycarbonyl
Trifluoroacetyl
Fluorenylmethyloxycarbonyl

The preparation of these synthetic antigens or allergens containing multiple alkyl or alkenyl carriers is illustrated below for a synthetic peptide whose side chain groups are blocked:

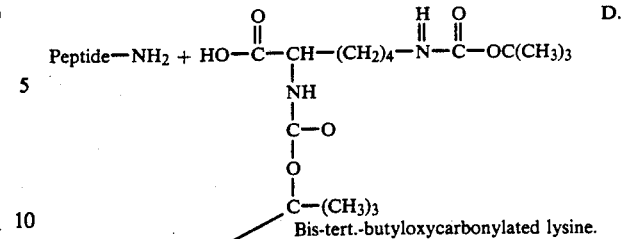

Bis-tert.-butyloxycarbonylated lysine.

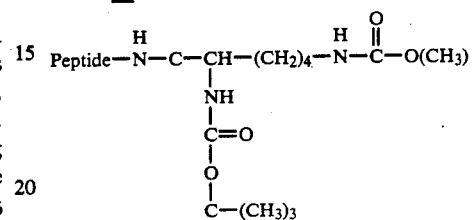

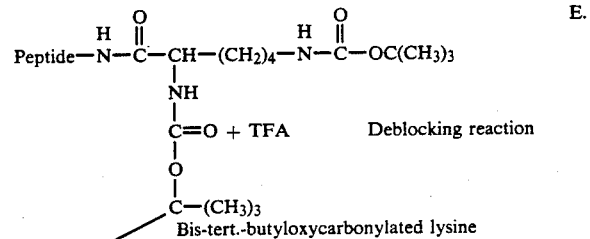

Bis-tert.-butyloxycarbonylated lysine

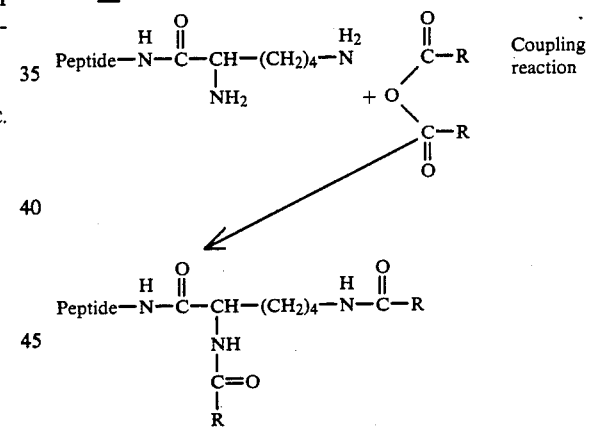

TFA = trifluoroacetic acid

Of course, the R groups can be the same or different since mixed anhydrides are suitable reactants.

It should be understood that in the above set of equations a lysine backbone joined the respective functional groups. Essentially any link between functional groups is suitable although it is preferred to minimize the presence of those groups which would impart toxicity to the vaccine or stimulate or prompt production of antibodies specific thereto, it being the purpose to produce antibodies to the synthetic peptide.

It is preferred that this link be an alkylene or alkenylene group, i.e., a bifunctional residue or radical of an alkane or alkene. These alkylene or alkenylene groups can be straight or branched chain and can have 2 to 6 carbon atoms.

DESCRIPTION OF SPECIFIC EMBODIMENTS

In the determination of the sequence of six amino acids which provide the H-epitope, it is preferred that more respective values than those set forth in the table below be assigned to respective amino acids in the protein antigen or allergen. Thus, there is set forth in the table below the broad, preferred and most preferred ranges to be assigned for the determination of six amino acids providing greatest local average hydrophilicity:

TABLE 2

| Amino Acid | Hydrophilicity Value | | |
|---|---|---|---|
| | Broad | Preferred | Most Preferred |
| Arginine | 3.0 | 3.0 | 3.0 |
| Aspartic Acid | 3.0 ± 1 | 3.0 ± .5 | 3.0 |
| Glutamic Acid | 3.0 ± 1 | 3.0 ± .5 | 3.0 |
| Lysine | 3.0 | 3.0 | 3.0 |
| Serine | 0.3 | 0.3 | 0.3 |
| Asparagine | 0.2 | 0.2 | 0.2 |
| Glutamine | 0.2 | 0.2 | 0.2 |
| Glycine | 0.0 | 0.0 | 0.0 |
| Proline | −.5 ± 1 | 0.0 ± .5 | 0.0 |
| Threonine | −0.4 | −0.4 | −0.4 |
| Alanine | −0.5 | −0.5 | −0.5 |
| Histidine | −0.5 | −0.5 | −0.5 |
| Cysteine | −1.0 | −1.0 | −1.0 |
| Methionine | −1.3 | −1.3 | −1.3 |
| Valine | −1.5 | −1.5 | −1.5 |
| Isoleucine | −1.8 | −1.8 | −1.8 |
| Leucine | −1.8 | −1.8 | −1.8 |
| Tyrosine | −2.3 | −2.3 | −2.3 |
| Phenylalanine | −2.5 | −2.5 | −2.5 |
| Tryptophan | −3.4 | −3.4 | −3.4 |

It will be recognized that these values are relative. By multiplying these values with a factor, one can obtain another set of values which can similarly be used to provide the same prediction and determination. The important concept is that the respective amino acids have the relative relationship as set forth in the table above. These arbitrary values are established for the purpose of providing a convenient means whereby the portion of a long chain protein molecule of highest hydrophilic characteristic is identified. When that is determined, the realization of the six amino acids accounting for that hydrophilicity peak is easily determined.

Thus the procedure of the invention can be employed to determine the sequence of six amino acids which provide the most hydrophilic region of numerous unrelated antigens.

Specifically, the hepatitis B surface antigen has been studied to determine the sequence of six amino acids which determine the H-epitope. The sequence of amino acids for such antigen is as follows:

Lys Pro Thr Asp Gly Asn (which correspond to amino acids 141-146 of the heptatis B surface antigen protein). Similarly, the sequence of amino acids for the human histocompatibility antigen HLA-B7 which determine the H-epitope is: Pro Arg Glu Glu Pro Arg (which correspond to amino acids 43-48 of the protein).

Similarly, the sequence of the amino acids for the influenze hemagglutinin antigen (X31 strain) which determine the H-epitope is: Val Glu Arg Ser Lys Ala (which correspond to amino acids 105-110 of the protein).

The H-epitope for the A/memphis/102/72 strain of influenza hemagglutinin is: Lys Arg Gly Pro Asp Ser, corresponding to amino acids 140 to 145 of the protein.

The H-epitopes for two other strains of influenza hemagglutinin, A/Eng/878/69 and A/NT/60/68/29c, are identical to the H epitope of A/memphis/102/72 as stated above.

The H-epitopes of the A/NT/60/68 and A/Qu/7/70 strains of hemagglutinin are identical and comprise the following amino acids: Arg Asn Val Pro Glu Lys corresponding to to amino acids 321-326 of the proteins.

The H epitope for the neuraminidase protein of the A/PR/8/34 strain of influenza is Arg Gly Arg Pro Lys Glu Lys, corresponding to amino acids 413 to 419 of the protein. This epitope contains seven amino acids because it comprises two adjacent and overlapping H-epitopes of equal hydrophilicity, as is the case for the Japan strain hemagglutinin already described (in the original manuscript).

The H-epitope for the diphtheria toxin fragment A is: Glu Thr Arg Gly Lys Arg, corresponding to amino acids 168 to 173 of the protein.

The H-epitope for the avian sarcoma virus gp 37 protein is: Leu Arg Glu Ile GLu Arg Leu, corresponding to amino acids 37 to 43 of the protein (again, two adjacent and overlapping H epitopes yielding, a seven amino acid sequence).

The H-epitope for the avian sarcoma virus src gene protein is: Lys Ser Lys Pro Lys Asp, corresponding to amino acids 5 to 10 of the protein.

The H-epitope for the E3/16 protein (external portion) of the adenovirus type 2 strain is: Lys Asp Lys Ile Gly Lys, corresponding to amino acids 40 to 45 of the protein.

The H-epitope for the Simian virus 40 VP1 protein is: Asp Asp Ser Pro Asp Lys Glu, corresponding to amino acids 77 to 83 of the protein (two adjacent and overlapping, H-epitopes).

The H-epitope for the available sequence of the fiber protein of adenovirus type 2 (N-terminal 80%) is: Asn Lys Asn Asp Asp Lys, corresponding to amino acids 393 to 398 of the protein.

The H-epitope of the Sindbis virus membrane glycoprotein E1 is: Ser Asp Arg Glu Gly Gln corresponding to amino acids 322 to 327.

The H-epitope of the Sindbis virus membrane glycoprotein E2 corresponds to the following amino acid chain: Asp Glu Ala Asp Asn corresponding to amino acids 36 to 41.

The H-epitope for the Sindbis virus membrane glycoprotein E3 corresponds to amino acids 27 to 32 and has the following sequence: Thr Arg Glu Pro Ser Arg.

The H-epitope for the foot and mouth disease virus capsid protein VP1 corresponds to amino acids 179 to 184 and has the following amino acid sequence: Arg Met Lys Arg Ala Glu.

There are two sequences of amino acids for the influenza hemagglutinin antigen (Japan strain) which determine H-epitopes of equivalent hydrophilicity i.e., they provide identical local average hyprophilicity. They are Glu Lys Glu Asn Pro Arg (correspond to amino acids 96-101) and Lys Glu Asn Pro Arg Asp (correspond to amino acids 97-102). Similarly, the sequence of amino acids for the influenza hemagglutinin antigen (Victoria A strain) which determine the H-epitope is: Asn Asp Asn Ser Asp Lys (corresponding to amino acids 188-193).

Similarly, there are two sequences of amino acids for the Fowl Plague virus hemagglutinin antigen which determine H-epitopes of identical local average hydrophilicity. They are: Glu Arg Arg Glu Gly Asn (corresponding to amino acids 97-102) and Arg Arg Glu Gly Asn Asp (corresponding to amino acid 98-103).

Similarly, the sequence of amino acids for the human chorionic Gonadotropin B subunit antigen which determine the H-epitope is: Arg Arg Ser Thr Thr Asp corresponding to amino acids 94-99.

Similarly, the sequence of amino acids for the Human Beta-2 microglobulin antigen which determines the H-epitope is: Pro Thr Glu Lys Asp Glu which corresponds to amino acids 73-78.

Similarly, the sequence of amino acids for the human Myelin basic protein antigen which determines the H-epitope. is: Gly Arg Asp Ser Arg Ser corresponding to amino acids 159–164.

Similarly, the sequence of amino acids for the Cholera Toxin B-chain antigen which determines the H-epitopes is: Glu Ala Lys Val Glu Lys corresponding to amino acids 79–84.

Another hepatitis B surface antigen has been studied to determine its sequence of six amino acids which determine the H-epitope. Its sequence is: Lys Pro Ser Asp Gly Asn corresponding to amino acid 141–146.

The sequence of amino acid for the *E. Coli* Heat Labile Toxin which determine the H-epitope is Glu Arg Met Lys Asp Thr corresponding to amino acids 66–71.

The sequence of amino acids for the *E. Coli* Heat Stable Toxin provides two identical H-epitopes whose amino acid sequence is Asp Ser Ser Lys GLu Lys and Ser Glu Lys Lys Ser Glu corresponding to amino acids 26–31 and 46–51, respectively.

The ragweed allergen Ra3 has an H-epitope whose amino acid sequence is Cys Thr Lys Asp Gln Lys corresponding to amino acid 88–93.

The ragweed allergen Ra5 has an H-epitope whose amino acid sequence is Ser Lys Lys Cys Gly Lys corresponding to amino acids 40–45.

The streptococcial M protein (strain 24) has two identical H-epitopes whose amino acid sequences are Arg Lys Ala Asp Leu Glu and Lys Ala Asp Leu Glu Lys corresponding to amino acids 58–63 and 59–64.

The trypanosoma brucei variant surface glycoprotein 117 has an H-epitope whose amino acid sequence is Lys Ala Lys Glu Lys Gly corresponding to amino acids 50–55.

In preparing vaccines according to the invention, it is preferred to attach to the six amino acids which define the H-epitope at least three amino acids on either side thereof. These three amino acids can be the same acids in the same sequences as they occur in the natural protein. However, other acids can also be used. For instance, in the hepatitis Bs vaccine the amino acid sequence can be Aba Aba Thr Lys Pro Thr Asp Gly Asn Aba Thr Aba (Aba residues have replaced Cys residues).

The synthetic vaccines are prepared as follows:

1. Chemical Synthesis: The Merrifield solid phase procedure is used to build up the appropriate sequence of 1-amino acids from the carboxyl terminal amino acid to the amino terminal amino acid and to add the fatty acid moiety(s) at the N-terminus. Starting with the appropriate carboxyl terminal amino acid attached to a polystyrene (or other appropriate) resin via chemical linkage to a chloromethyl group, benzhydrylamine group, or other reactive group of the resin, amino acids are added one by one using the following procedure for each:

a) Peptidyl resin is washed with methylene chloride b) neutralized by mixing for 10 min. at room temperature with 5% (v/v) diisopropylethylamine (or other hindered base) in methylene chloride c) washed with methylene chloride.

d) An amount of amino acid or fatty acid equal to six times the molar amount of the growing peptide chain is activated by combining it with onehalf as many moles of a carbodiimide (e.g. dicyclohexylcarbodiimide, diisopropylcarbodiimide) for 10 minutes at 0° C., to form the symmetric anhydride of the amino acid or fatty acid. The amino acid used should be provided originally as the N-α-butyl-oxycarbonyl derivative, with side chains protected with benzyl esters (aspartic and glutamic acids) benzyl ethers (serine, threonine, cysteine, tyrosine), benzyl oxycarbonyl groups (lysine) or other protecting groups commonly used in peptide synthesis. Fatty acids require no protecting groups.

e) the activated amino acid or fatty acid is reacted with the peptide resin for 2 hours at room temperature, resulting in addition of the new amino acid or fatty acid to the end of the growing peptide chain.

f) The resin is washed with methylene chloride g) The N-α-(butyloxycarbonyl group is removed from the most recently added amino acid by reacting with 30% (v/v) trifluoroacetic acid in methylene chloride for 30 minutes at room temperature.

h) The resin is washed with methylene chloride.

i) Steps a through h are repeated until the required peptide sequence has been constructed, with the fatty acid being put in place last.

The peptide is then removed from the resin, and simultaneously the side-chain protecting groups are removed, by reacting with anhydrous hydrofluoric acid containing 10% (v/v) of anisole. Subsequently, the peptide can be purified by gel filtration, ion exchange or high pressure liquid chromatography, or other suitable means.

In some cases, chemical synthesis can be carried out without the solid phase resin, in which case the synthetic reactions are performed entirely in solution. The reactions, and the final product, are otherwise essentially identical.

The synthetic vaccines of the invention can readily be incorporated into compositions possessing an oily adjuvant such as Freund's adjuvant (complete or incomplete) or into lipsomes due to their lipophilic nature which causes them to be retained in these adjuvants longer. This longer retention time facilitates the desired immune response.

When two fatty acid or similar moieties are desired as carriers for the peptide, it is preferred that the synthetic vaccine be formed using the following technique. Thus, the N-terminal end of the peptide, while still on the Merrifield resin, is coupled to a lysine moiety or other suitable linking bridge possessing diaminoalkylene or-alkenylene moiety. The lysine, which contains two amino groups, is linked to the N-terminal end of the peptide using, for instance, bis-tertiary butyloxycarbonylated lysine as reactant as set forth above. After deprotection, both the alpha and the epsilon amino groups are available for fatty acid coupling. Treatment as above yields the fatty acid disubstituted lysyl peptide, which thereafter can be cleaved from the resin with hydrofluroic acid. This derivative should be retained to a greater extent by Freund's adjuvant or liposome, and form more stable self-aggregates.

A simple variation of this approach can be used to place one (or more) fatty acids at the C-terminus of the peptide. A lysine residue can be coupled to the Merrifield resin as the first step of the synthesis. This lysine can be differentially protected, for example, as the alpha-tertiary butyloxycarbonyl, epsilon-9-flurenylmethyloxycarbonyl derivative, allowing selective deprotection of the epsilon amino group by treatment with piperidine/methylene chloride (1:1) at 25° C. for 30 minutes. A fatty acid or other lipophilic substance may then be coupled by the same procedure used in coupling fatty acids to the N-terminus of the peptide. Thereafter, the alpha-tertiary butyloxycarbonyl group is removed by the usual acid treatment, and peptide synthesis is completed by the usual procedures. If two or more alpha-tertiary butyloxycarbonyl, epsilon-9-fluorenylmethyloxycarbonyl lysines are sequentially treated as above, a product can be generated that bears multiple fatty acid substituted lysines at its C-terminus.

It is possible, by the procedures described above, to make antigenic peptide - fatty acid conjugates wherein there exist one or multiple fatty acid residues at the N-terminus of the peptide, at the C-terminus of the peptide, or at both ends simultaneously. Although lysine is used in the example above, it is understood that any diamino acid could be used, including such amino acids as ornithine, or alpha-, gamma-diamino butyric acid.

In order to more fully illustrate the invention and the manner of practicing the same, the following examples are presented.

EXAMPLE 1

Coupling of a Palmityl Moiety to Glycyl Hepatitis B Antigenic Peptide (H Peptide)

An initial acid solution comprising 3 parts trifluoroacetic acid and 7 parts methylene chloride was formed. There was also formed a base solution comprising 5 parts diisopropylethylamine and 95 parts methylene chloride. Merrifield resin was used as starting material. Specifically the starting material was commercially available tertiary butyloxycarbonylated glycyl resin ester containing 0.33 m moles of glycine per gram of resin.

Glycyl H peptidyl resin. The H peptide was constructed on 1 gram of butyloxycarbonylated glycyl resin by the classical Merrifield method. Its structure was Gly Gly Gly Aba Aba Thr Lys Pro Thr Asp Gly Asn Aba Thr Aba Gly Resin, with amino acid side chains protected as follows: Thr benzyl ether, Lys carbobenzoxy amide, and Asp benzyl ester.

In this synthesis, an N-terminal Gly Gly Gly sequence was added to act as a spacer to separate the palmityl moiety from the rest of the peptide. Palmitic acid was coupled to the N-terminal glycyl residue as follows:

1. The N-terminal tertiary butyloxycarbonyl group was removed by 30 min (25° C.) treatment with acid solution as in the Merrifield procedure.
2. The newly exposed alpha amino group was neutralized by treatment with base solution for 10 min (25° C.), again, as in the Merrifield procedure.
3. Three equivalents (1 m mole) of palmitic anhydride was dissolved in 15 ml of methylene chloride, and reacted with the peptidyl resin. The reaction was complete after 2 hrs. (25° C.) as determined by the Kaiser ninhydrin test, which became negative at that time.
4. The palmityl H peptide was cleaved from the resin, and all blocking groups were removed, by treatment with hydrofluoric acid/anisole (9/1) for 15 minutes at 0° C. The palmityl H peptide was extracted from the resin beads by sequential washing with flacial acetic acid, acetic acid/water (50/50), and with water. Washes were pooled and lyophilized.
5. The crude product was purified by extraction with $MeCl_2$ to remove traces of anisole and lipid contaminants.
6. The product was dissolved in glacial acetic acid, although it is preferred to employ dimethylsulfoxide, then diluted with 9 parts water. This causes the immediate formation of a microemulsion of the peptide, which can be observed as an opalescent appearance of the solution. This material was lyophilized, and resuspended in phosphate buffered saline for immunizations.

EXAMPLE 2

Coupling of Two Palmityl Moieties to Lysyl Hepatitis B Antigenic Peptide (H Peptide)

Lysyl H peptidyl resin: This peptide was constructed on 1 gram of tertiary butyloxycarbonylated glycyl resin by the Merrifield method. Its structure was: Lys Gly Gly Aba Aba Thr Lys Pro Thr Asp Gly Asn Thr Aba Gly Resin, with amino acid side chains protected as follows: Thr benzyl ether, N-terminal Lys alpha and epsilon tertiary butyloxycarbonyl, central Lys epsilon carbobenzoxy amide, and Asp benzyl ester.

Palmitic acid was coupled to the alpha and epsilon amino groups of the N-terminal lysyl residue as follows:

1. The N-terminal tertiary butyloxycarbonyl and epsilon tertiary butyloxycarbonyl groups were removed by 30 min. (25° C.) treatment with acid solution as in the Merrifield procedure.
2. The newly exposed alpha and epsilon amino groups were neutralized by treatment with base solution for 10 min. (25° C.).
3. Three equivalents (1 m mole) of palmitic anhydride were dissolved in 15 ml of $MeCl_2$, and reacted with the peptidyl resin. The reaction was stopped after 2 hours (25° C.) but was only about 80% complete as determined by the Kaiser ninhydrin test. Therefore, a second coupling under identical conditions was carried out. After this coupling, the ninhydrin test was negative, indicating complete coupling of palmitic acid to both the alpha and epsilon amino groups of the N-terminal lysyl residue.
4. The product was cleaved from the resin and purified as in steps 4 through 6 of Example 1.
5. The results of a preliminary immunization study using rabbits are shown in Table I. These results show that the conjugate is capable of producing anti-HbsAg responses with or without use of an adjuvant, although the highest titers were obtained with adjuvant present.

TABLE I

| Rabbit I.D. # | Pre-immune | Titer (days after initial inoculation) | | |
|---|---|---|---|---|
| | | 20 | 37 | 54 |
| 657 | 0 | 0 | 1.9 | 41.5 |
| 658 | 2.8 | 74.2 | — | — |

TABLE I-continued

| Rabbit I.D. # | Pre-immune | Titer (days after initial inoculation) | | |
|---|---|---|---|---|
| | | 20 | 37 | 54 |
| 659 | 3.0 | 3.3 | 52.0 | 52.3 |
| 661 | 5.2 | 4.5 | 11.0 | 15.1 |
| 662 | 0.6 | 0.6 | 2.9 | 2.9 |

Immunizations were given on days 1 and 23. These consisted of 0.5 ml of Freund's complete adjuvant emulsified in 0.5 ml of phosphate-buffered saline for rabbits 657-659, and 1 ml of phosphate-buffered saline without adjuvant for 661 and 662. Each dose contained 0.05 mg dipalmityl H peptide on day 1 and 0.2 mg on day 23. Titers were determined by the Ausab test (Abbott Laboratories); titers over 10.0 were commonly considered to represent immunity to type B hepatitis.

The data above reveals that the antibody titer of test animals is dramatically increased when a synthetic vaccine of the invention containing an alkyl or alkenyl carrier is administered to the host animal.

By the procedure of the invention there is realized a vaccine which is characterized by the absence of an amino acid sequence of the entire protein antigen or allergen. For instance, in the case of a hepatitis B vaccine, the vaccine is free of other peptide sequences of the hepatitis B surface antigen protein, or other proteins found in the virion. Vaccines can be synthesized which are free of biologically produced components, free of viral components whether they be active or inactive, free of antibodies, free of deoxyribonucleic acid (DNA) and free of lipids, and ar therefore likely to be substantially free from undesirable side effects commonly found with other vaccines (unintentional infection with virus, allergic reaction, fevers, etc.).

The synthetic vaccines are characterized by exceptional specificity and evoke an unusual and special response when introduced into a host animal. Whereas a vaccine made of natural material and introduced into a host animal usually evokes an immunological response by the creation of antibodies specific to a number of distinct epitopes present on the antigens found in that vaccine, when the vaccine of the present invention is introduced into a host animal, it causes the formation of antibodies which are mono-specific, i.e., are specific to the single antigenic site on the vaccine. Thus, the vaccines of the present invention can be employed to form immune globulin comprising a mono-specific antibody. These mono-specific antibodies may be produced in animals, to serve as a source for diagnostic immunoglobulin to be used in serological testing, for example in identifying strain types of pathogenic organisms isolated from infected individuals.

In the preparation of a vaccine the concentration of the same in the physiologically acceptable medium will vary depending on the number and types of H epitopes contained therein. Generally speaking, the active component of the vaccine can be present in a concentration which is lower than the concentration of active material in known vaccines since in the known vaccines higher concentrations were required in order to have present the required number of antigenic determinants to evoke the desired immunological response. The vaccine concentration will, of course, vary from vaccine to vaccine. Generally speaking, its concentration will be from 5 to 100 u gm, preferably 20 to 50 u gm per dose to give suitable immunogenicity. It is particularly contemplated to use the vaccine in a dosage of 0.01 to 100, especially 0.01 to 10 micrograms per dose.

The vaccine will have sufficient potency to provide an antibody titer of at least 1:100 when determined by tests such as passive hemaglutination. For instance, the vaccines of hepatitis $B_s$ have an antibody $HB_s$ titer of at least 1:100 when determined by passive hemaglutination (standardized by tests on a frozen anti-serum control) in at least four chimpanzees immunized with two doses of the standard vaccine in accordance with the recommended schedule, the anti-$HB_s$ remaining detectable at a titer greater than 1:10 for at least a year following the onset of immunization of the chimpanzees. Naturally, the vaccine concentration can vary from these concentrations depending upon the effect desired.

The vaccine can be administered by subcutaneous or intramuscular injection. While the preferred route would depend upon the particular vaccine, it is believed that intramuscular injection will be generally suitable. Frequency of administration will vary depending upon the vaccine and the nature and type of epitopes and their concentration in the active component. Generally speaking, the vaccine will be administered in two doses about one month apart followed by a booster at six months to one year after primary immunization. Of course, the dosage will depend upon the size of the host animal being inoculated. The subsequent doses or the booster will depend on the level of antibody in the blood as a result of the initial immunization. Licensable adjuvants conventionally employed in vaccine manufacture can be utilized.

In the case of a hepatitis vaccine as particularly contemplated herein, the same is recommended for all persons at risk of developing hepatitis B infection and particularly those at especially high risk such as patients and staff on hemodialysis unit, medical personnel, persons of tropical populations and those visiting the tropics. In the case of tropical populations, particularly in Africa, Asia, the Mediterranean region and South America, where high incidence of hepatitis B infections has been consistently observed, the vaccine should be administered sufficiently early in life to prevent acquisition of chronic carrier state infection which tend to occur in these regions within the first five years of life. In fact, the vaccine is useful for all persons not already protected against hepatits B infections as a result of prior immunity.

What is claimed is:

1. A synthetic antigen comprising a carrier coupled to a peptide residue,
    (a) the peptide residue having an N terminal amino group and a C terminal carboxy group, said peptide residue comprising a naturally occurring sequence of at least six amino acids, said peptide residue containing an epitope and being coupled to the carrier which comprises
    (b) one or more alkyl or alkenyl fatty acid groups having at least 12 carbon atoms, said coupling occurring at a site selected from the group consisting of
        (i) one or more of said fatty acid groups being coupled to one or more functional groups of a polyfunctional group which is bound to the N-terminal amino group of the peptide residue,
        (ii) one or more of said fatty acid groups being coupled to one or more functional groups of a polyfunctional group which is bound to the C-terminal carboxy group of the peptide residue, (iii) one of said fatty acid groups being coupled to the N-terminal amino group of the peptide residue and one or more of said fatty acid groups being coupled to one or more functional groups of a polyfunctional group which is bound to the C-terminal carboxy group of the peptide residue, and (iv) one or more of said fatty acid groups being coupled to one or more functional groups of a polyfunctional group which is bound to the N-terminal amino group of the peptide residue and one or more of said fatty acid groups being coupled to one or more functional groups of a polyfunctional group which is bound to the C-terminal carboxy group of the peptide residue.

2. An antigen according to claim 1, wherein the fatty acid group has 12 to 36 carbon atoms.

3. An antigen according to claim 1, wherein the fatty acid group has 12 to 24 carbon atoms.

4. An antigen according to claim 1, wherein the fatty acid is selected from the group consisting of palmitic acid, stearic acid, behenic acid, oleic acid and mycolic acid.

5. An antigen according to claim 1, wherein the polyfunctional group is a polyamino group.

6. An antigen according to claim 5, wherein the polyamino group is a diamino group.

7. An antigen according to claim 6, wherein one or two or said fatty acid groups is coupled to one or both amino groups of a diamino group which is bound to the N-terminal amino group of the peptide residue.

8. An antigen according to claim 6, wherein one or two or said fatty acid groups is coupled to one or both amino groups of a diamino group which is bound to the C-terminal carboxy group of the peptide residue.

9. An antigen according to claim 6, wherein one of said fatty acid groups is coupled to the N-terminal amino group of the peptide residue and one or two of said fatty acid groups is coupled to one or both amino groups of a diamino group which is bound to the C-terminal carboxy group of the peptide residue.

10. An antigen according to claim 6, wherein one or two of said fatty acid groups is coupled to one or both amino groups of a diamino group which is bound to the N-terminal amino group of the peptide residue and one or two of said fatty acid groups is coupled to one or both amino groups of a diamino group which is bound to the C-terminal carboxy group of the peptide residue.

11. An antigen according to claim 1, wherein the peptide residue is a synthetic peptide.

12. An antigen according to claim 1, wherein the peptide residue comprises an H-epitope of a protein antigen or allergen.

13. An antigen according to claim 6, wherein the diamino group is selected from the group consisting of lysine; ornithine and alpha, gamma diamino butyric acid.

14. A synthetic antigen comprising a carrier coupled to a peptide residue,
(a) the peptide residue according to claim 1 additionally having side chain amino groups in addition to an N-terminal amino group, and being coupled to the carrier which comprises
(b) one or more alkyl or alkenyl fatty acid groups having at least 12 carbon atoms, said coupling occurring only at the N-terminal amino group of said peptide residue.

15. An antigen according to claim 14, wherein the fatty acid group has 12 to 36 carbon atoms.

16. An antigen according to claim 14, wherein the fatty acid group has 12 to 24 carbon atoms.

17. An antigen according to claim 14, wherein the alkyl or alkenyl fatty acid group is coupled to the N-terminal amino group of the peptide residue via a carbonyl group.

18. An antigen according to claim 14, wherein the alkyl or alkenyl fatty acid group is coupled directly to the N-terminal amino group of peptide residue.

19. An antigen according to claim 14, wherein the fatty acid is selected from the group consisting of palmitic acid, stearic acid, behenic acid, oleic acid and mycolic acid.

20. An antigen according to claim 14, wherein the peptide residue is a synthetic peptide.

21. An antigen according to claim 14, wherein the peptide residue comprises an H-epitope of a protein antigen or allergen.

* * * * *